(12) United States Patent
Jeys et al.

(10) Patent No.: US 6,194,731 B1
(45) Date of Patent: Feb. 27, 2001

(54) BIO-PARTICLE FLUORESCENCE DETECTOR

(75) Inventors: Thomas H. Jeys; Antonio Sanchez, both of Lexington, MA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/197,540

(22) Filed: Nov. 12, 1998

(51) Int. Cl.[7] .................................................. G01N 21/64

(52) U.S. Cl. ............................................................ 250/461.2

(58) Field of Search ........................................... 250/461.2

(56) References Cited

U.S. PATENT DOCUMENTS 5,471,294 * 11/1995 Ogino ....................................... 356/73
5,895,922 * 4/1999 Ho ....................................... 250/491.2

\* cited by examiner

*Primary Examiner*—Constantine Hannaher
(74) *Attorney, Agent, or Firm*—Thomas C. Stover

(57) ABSTRACT

Biological aerosols are detected in real time by passing air, which may contain the aerosols, through a duct having a pair of photodetectors adjacent the duct for detecting fluorescence of the aerosols produced by ultraviolet laser beam illumination of the airflow. A pair of opposed mirrors, make the effective sample air volume large, by producing multiple ultra-violet beam illumination paths through adjacent portions of the duct for each single pulsed beam, in turn increasing the magnitude of the detected fluorescence signal.

16 Claims, 1 Drawing Sheet

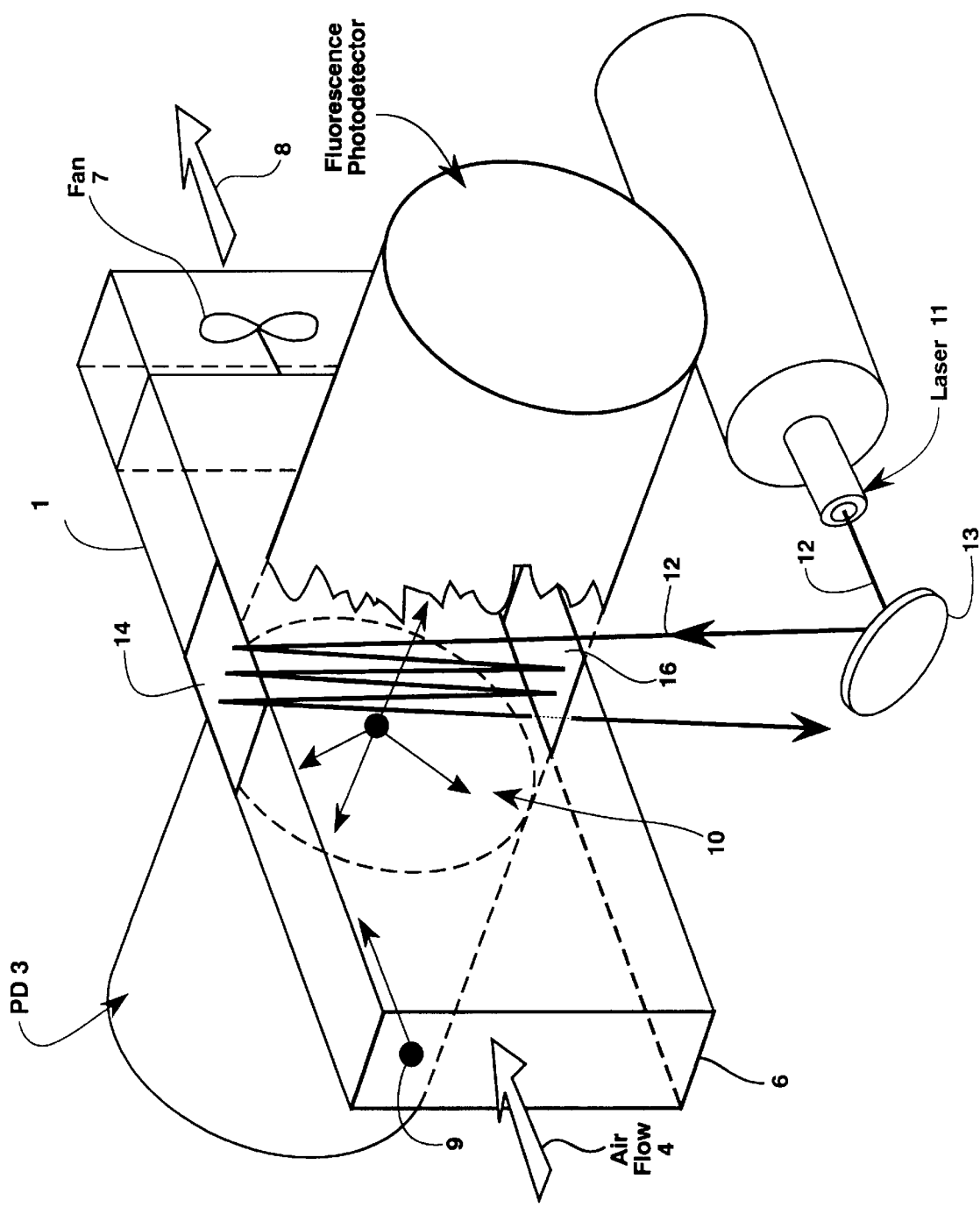

BIO-PARTICLE FLUORESCENCE DETECTOR

STATEMENT OF GOVERNMENT INTEREST

This invention herein may be manufactured or used by or for the Government for governmental purposes without the payment of any royalties thereon.

BACKGROUND OF THE INVENTION

The present invention relates to the field of the detection of biological aerosols.

Laser based systems are known for the detection of airborne particles of destructive biological particles such as harmful bacteria, individual or groups of cells, or protein particles. In a prior art method, a laser light illuminates air drawn through a duct which may bear the particles to be detected, such light having a wavelength near or at the peak of an absorption resonance in trace gases or chemical elements to be detected. A photodetector responds to the resulting radiation of fluorescent light due to the laser induced biochemical fluorescence. See for example, FIG. 1, col. 4–5, of U.S. Pat. No. 4,651,010 to Javan. As mentioned in this patent, it is also known to pulse the illuminating laser beam and gate the receiver coupled to the photodetector to cause it to respond in a delayed manner during a short period following each laser illumination pulse. The delay is fashioned to take advantage of the fluorescence decay time of the agent to be detected, so as to discriminate against false ambient illumination.

It is desired to improve the prior art method mentioned in the Javan patent, of laser illuminating air carrying the particles to be detected, which has been drawn through a duct, to detect the aforesaid fluorescence produced by the illuminating laser beam.

BRIEF SUMMARY OF A PREFERRED EMBODIMENT OF THE INVENTION

The effective sample volume of air passing through the aforesaid duct is greatly increased by multiply passing a pulsed illuminating laser beam several times through several different portions of the volume of air passing through the duct, this operation being facilitated by opposed mirrors positioned within the duct. Thus, the mirrors cause the pulsed beam to follow several multiple paths through the duct to increase the number of particles hit by the beam, and detected by a pair of photodetectors positioned alongside the duct. As a result, a large volume of air is sampled for a duct of relatively small size, and the magnitude of the detected fluorescent light signals is accordingly increased.

BRIEF DESCRIPTION OF THE DRAWING

Other features and advantages of the invention will become more apparent upon reading the following description taken in conjunction with the sole FIGURE, schematically illustrating a preferred embodiment of the invention.

DETAILED DESCRIPTION OF A PREFERRED EMBODIMENT OF THE INVENTION

In the sole FIGURE, duct 1 is disclosed having a pair of fluorescence photodetectors 2 and 3, straddling the duct. Exhaust fan 7 draws atmospheric air into a duct inlet 6 as indicated by arrow 4, and ejects air from the duct as indicated by arrow 8. Illuminating laser 11 directs a low intensity pulsed ultraviolet beam 12 at a first mirror 14, via reflector 13, which mirror 14 faces a second opposed mirror 16 as shown.

If the undesirable agents such as particles 9 are present in the air drawn through the duct, laser-induced bio-chemical fluorescence indicated at 10, will be detected by the suitably filtered fluorescence photodetectors as known in the art. The mirrors 14 and 16 constitute light beam path multiplying means for causing beam 12 to pass back and forth several times within the duct through adjacent air volume duct portions. This is facilitated by directing beam 12 at mirror 14 at an angle slightly greater than ninety degrees as shown in the FIGURE, to cause the beam to "walk" across the duct.

These biologic agent detectors can beneficially be "throwaway" units to enable them to be widely dispersed in various areas under surveillance. Since the cost of production thus becomes more significant, it is desirable to use small low powered solid state lasers. This is facilitated since the laser power can be low due to the multiplying effect of the illuminating beam path of the invention which increases the amplitude of the signal to be detected over ambient noise levels.

Other embodiments of the invention will become apparent to workers in the art, and thus the scope of the invention is to be restricted to the terms of the following claims and art recognized equivalents thereof. For example, it is conceivable that a light source other than a pulsed laser could be used. The described apparatus could be placed within an artillery shell as shown in FIG. 3 of the aforesaid prior art patent, which would eliminate the exhaust fan.

What is claimed is:

1. A biologic agent detector for detecting agents in the atmosphere comprising:
    (a) means for drawing air which may contain said agents through a duct;
    (b) illumination means for illuminating the air within said duct with a laser beam;
    (c) photodetector means for detecting fluorescence of biologic agents within the air drawn through said duct produced by operation of said illumination means; and
    (d) laser beam path multiplying means for causing said laser beam to pass back and forth through said duct through seperate portions of the interior of said duct.

2. The detector of claim 1 wherein said laser beam path multiplying means comprises light beam reflector means.

3. The detector of claim 2 wherein said light beam reflector means includes first and second mirrors positioned to intercept light at separated portions of said duct.

4. The detector of claim 3 wherein said illumination means causes said laser beam to be initially directed at one of said mirrors at an angle slightly greater than ninety degrees.

5. The detector of claim 4 wherein said illumination means comprises a low intensity pulsed laser.

6. The detector of claim 3 wherein said illumination means comprises a low intensity pulsed laser.

7. The detector of claim 2 wherein said illumination means comprises a low intensity pulsed laser.

8. The detector of claim 1 wherein said illumination means comprises a low intensity pulsed laser.

9. A biologic agent detector for detecting agents in the atmosphere comprising:
    (a) means for drawing air which may contain said agents through a duct;

(b) illumination means for illuminating the air within said duct with an ultraviolet laser beam;

(c) photodetector means for detecting laser-induced biochemical fluorescence of biologic agents, within the air drawn through said duct, produced by operation of said illumination means; and (d) laser beam path multiplying means for causing said laser beam to pass back and forth through said duct through seperate portions of the interior of said duct.

10. The detector of claim 9 wherein said laser beam path multiplying means comprises light beam reflector means.

11. The detector of claim 10 wherein said light beam reflector means includes first and second mirrors positioned to intercept light at separated portions of said duct.

12. The detector of claim 11 wherein said illumination means causes said laser beam to be initially directed at one of said mirrors at an angle slightly greater than ninety degrees.

13. The detector of claim 12 wherein said illumination means comprises a low intensity pulsed laser.

14. The detector of claim 11 wherein said illumination means comprises a low intensity pulsed laser.

15. The detector of claim 10 wherein said illuminination means comprises a low intensity pulsed laser.

16. The detector of claim 9 wherein said illumination means comprises a low intensity pulsed laser.

* * * * *